United States Patent [19]

El Gazayerli

[11] Patent Number: 5,139,038

[45] Date of Patent: Aug. 18, 1992

[54] DENTAL FLOSSING INSTRUMENT

[76] Inventor: Mohamed M. El Gazayerli, 476 Steeple Chase, Bloomfield Hills, Mich. 48013

[21] Appl. No.: 676,291

[22] Filed: Mar. 28, 1991

[51] Int. Cl.$^5$ .............................................. A61C 15/00
[52] U.S. Cl. .................................. 132/325; 132/324; 132/326
[58] Field of Search ............... 132/323, 324, 325, 326, 132/327

[56] References Cited

U.S. PATENT DOCUMENTS

| | | | |
|---|---|---|---|
| 1,105,005 | 7/1914 | Sonn | 132/327 |
| 2,176,069 | 10/1939 | Goulet | 132/327 |
| 2,873,749 | 2/1959 | Gjerde | 132/327 |
| 3,236,247 | 2/1966 | Brockman | 132/323 |
| 4,094,328 | 6/1978 | Ray | 132/325 |
| 4,404,978 | 9/1983 | Withers | 132/323 |
| 4,508,125 | 4/1985 | Loubier | 132/326 |
| 4,655,233 | 4/1987 | Laughlin | 132/323 |
| 4,691,719 | 9/1987 | Ciccarelli | 132/325 |
| 4,807,651 | 2/1989 | Naydich | 132/323 |
| 4,832,062 | 5/1989 | Grollimund et al. | 132/327 |

*Primary Examiner*—Gene Mancene
*Assistant Examiner*—Frank A. LaViola
*Attorney, Agent, or Firm*—Reising, Ethington, Barnard, Perry & Milton

[57] ABSTRACT

An instrument (10) is provided for manipulating a length of dental floss (18) so as to allow for simultaneous cleaning of the sides and the rear of a tooth. The instrument (10) comprises a handle (12) having a channel (14) therein. A pair of prongs (20) extend away from the handle (12) to distal ends that define an axis therebetween. The prongs (20) hold a length of floss (18) between their respective distal ends along the axis. A slide member (28), having a floss engaging member (32) pivotally secured thereto, is slidably retained in the channel (14) for movement along a slide axis located between and extending perpendicular to the prong-defined axis. The slide member (28) moves along the slide axis between a retracted position and an extended position. As the slide member (28) moves to the extended position, the floss engaging member (32) pivots to a floss-engaging position transverse to the slide axis for engaging the length of floss (18) so as to reconfigure the length of floss (18) to a bowed configuration. The floss (18) in the bowed configuration is positioned about the tooth to be cleaned so that the floss is proximate the rear and sides of the tooth. The slide member (28) is then returned to the retracted position so as to release the floss (18) and leave the floss positioned about the tooth. The floss is now in position to simultaneously clean the sides and the rear of the tooth when the instrument handle is suitably manipulated.

18 Claims, 3 Drawing Sheets

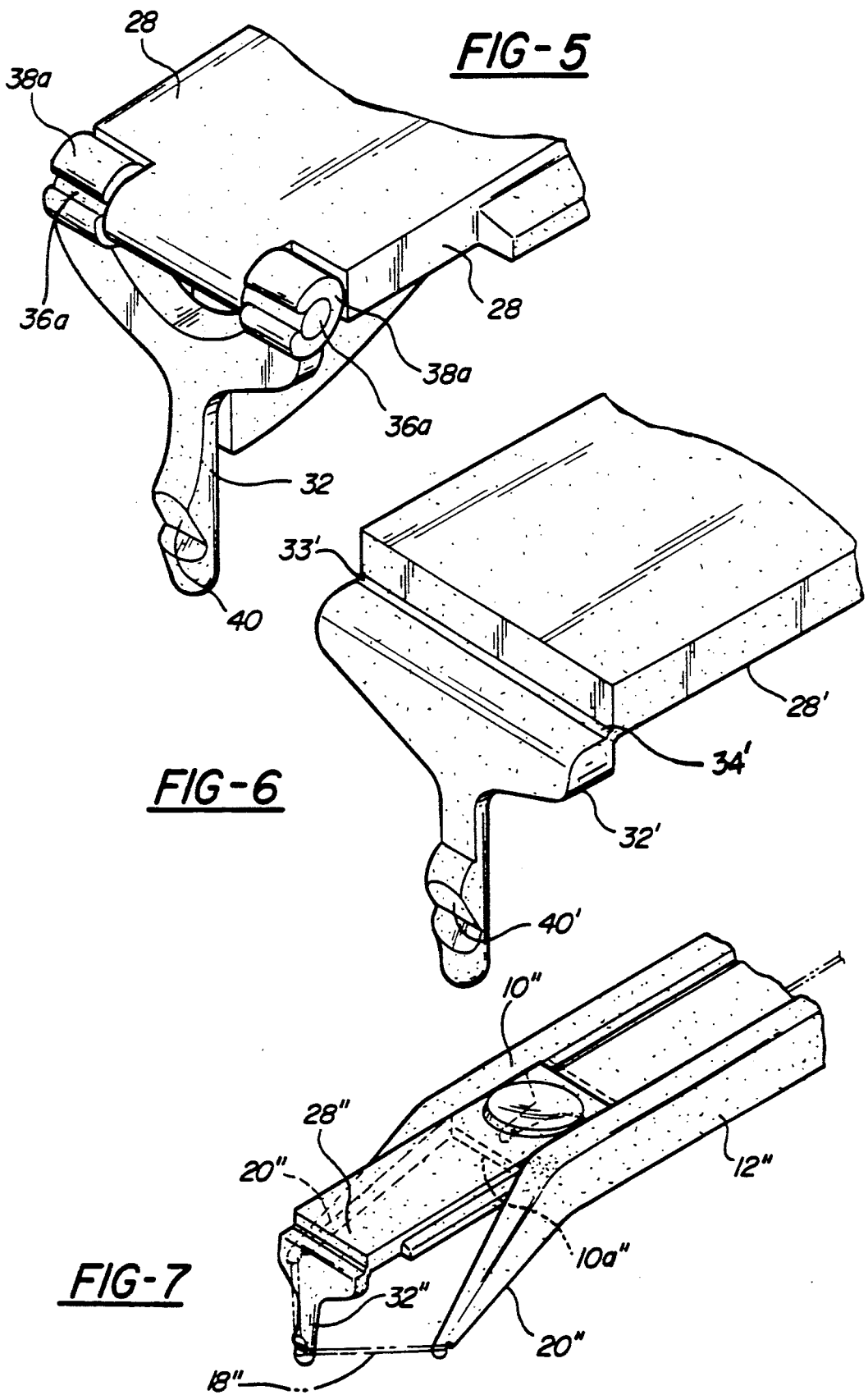

DENTAL FLOSSING INSTRUMENT

BACKGROUND OF THE INVENTION

1. Field of the Invention

The subject invention relates to a dental flossing instrument. Specifically, the subject invention relates to an instrument for manipulating dental floss to allow a user to simultaneously floss the rear and sides of a tooth to be cleaned.

2. Description of the Prior Art

Flossing between teeth is an accepted practice for cleaning between the teeth and gums to reduce the incidence of tooth and gum disease. Typically, the dental floss is held in tension between an individual's fingers and placed between adjacent teeth. With the floss so positioned between the teeth, it is repeatedly moved up and down between the side of the tooth and the adjacent gum to remove plaque and other debris.

This manual procedure has been supplanted by certain prior art devices which hold the dental floss in the tensioned position for the user. For example, U.S. Pat. No. 4,094,328 to Ray issued Jun. 13, 1978 discloses such an instrument. The instrument shown holds the dental floss in tension between spaced apart prongs on one end thereof. The prongs are inserted into the mouth such that the floss is placed between the sides of the adjacent teeth. The instrument is then reciprocated up and down to move the floss in a manner to clean between only one side surface of the tooth and the adjacent gum.

Other flossing devices are known for simultaneously cleaning between opposite sides of a tooth and the adjacent gum. For example, U.S. Pat. No. 4,404,978 to Withers issued Sep. 20, 1983 discloses a flossing device having a pair of spaced apart prongs for holding two, parallel lengths of dental floss between each pair of prongs. The prongs are inserted into the user's mouth and the dental floss is located adjacent the tooth side to be cleaned. The handle is then released allowing the dental floss to be tensioned around the opposite sides of the tooth to be cleaned.

Similarly, U.S. Pat. No. 4,832,062 to Grollimund et al issued May 23, 1989 discloses a device for simultaneously cleaning sides of adjacent teeth simultaneously. The device allows the sides of two different adjacent teeth to be simultaneously cleaned with dental floss.

The prior art flossing devices described above are deficient in that they are limited to cleaning, at the most, only two sides of the same tooth or different teeth at a time. Each device requires a number of lengths of floss corresponding to the number of tooth surfaces to be cleaned. The construction of such flossing devices is thus quite complex (e.g. requiring two pairs of prongs) and costly. Moreover, the prior art flossing devices are not adapted for cleaning between the back or rear of the tooth and adjacent gum where accessibility is limited and difficult.

SUMMARY OF THE INVENTION AND ADVANTAGES

According to the present invention, there is provided a dental flossing instrument to allow a user to simultaneously floss two sides and the rear of a tooth to be cleaned. The instrument comprises a handle and fork means extending from the handle in a manner to hold a length of the floss in a generally linear configuration along an axis defined by the fork means. The instrument also comprises floss manipulating means slidably disposed on the handle for movement transverse to the axis between a first retracted position out of engagement with the length of floss and a second extended position for engagement with the length of floss to reconfigure it to a bowed configuration amenable for positioning about two sides and the rear of the tooth to be cleaned.

Preferably, the floss manipulating means includes a floss engaging means pivotably mounted thereon so as to be oriented transverse to the axis when the floss manipulating means is moved toward the extended position for engaging the length of floss. The floss engaging means is pivotable to release the length of floss and overlie the handle as the floss manipulating means is returned to the retracted position.

Accordingly, there is provided a dental flossing instrument which allows a single length of floss to be reconfigured, or reshaped, to simultaneously clean two sides and the rear of a tooth.

BRIEF DESCRIPTION OF THE DRAWINGS

Other advantages of the present invention will be readily appreciated by reference to the following detailed description when considered in connection with the accompanying drawings wherein:

FIG. 5 is an enlarged, partial perspective view of the pivoted hinqe connection between the slide member end and the floss engaging member;

FIG. 6 is an enlarged, partial perspective view of an alternative "live-hinge" between the slide member and the floss engaging member; and FIG. 7 is a perspective view, partially broken away, showing an alternative prong configuration.

DETAILED DESCRIPTION OF THE INVENTION

Figure 1:
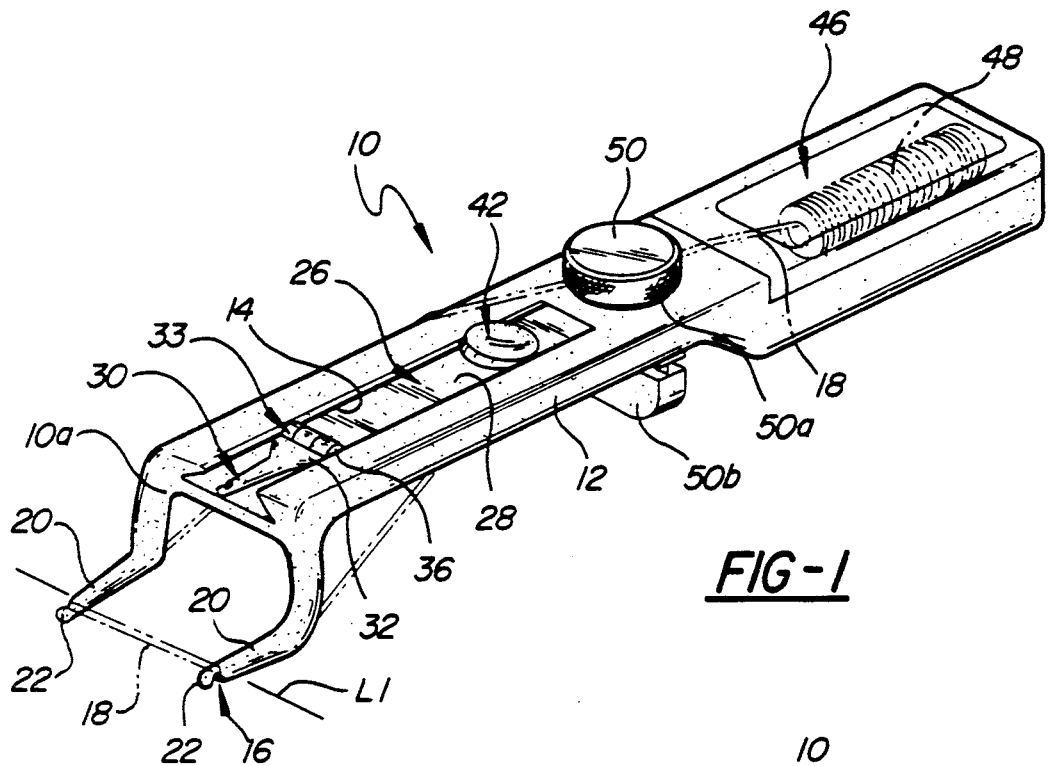
FIG. 1 is a perspective view of a dental flossing instrument in accordance with the embodiment of the invention.

A dental flossing instrument in accordance with one embodiment of the invention to allow a user to simultaneously floss two sides and the rear of a tooth to be cleaned is generally shown at 10 in the Figures. The instrument 10 includes an elongated handle 12 having a channel 14 extending longitudinally from handle end 10a. The channel 14 terminates at a location short of the other opposite handle end (not shown) so that a stop shoulder 10b is formed closing off the channel 14 for purposes to be described below. The channel 14 extends along the top surface of the handle 12.

The handle 12 includes fork means generally indicated at 16 extending away from the handle 12 and adapted for holding a length of dental floss 18 in a generally linear configuration therebetween along a first axis L1. More specifically, the fork means 16 comprises a pair of spaced prongs 20 which are preferably integral with the handle 12 and define the axis L1 therebetween. Each of the prongs 20 extends downwardly or depends from the handle 12 and further extends longitudinally away from the handle 12 to respective distal ends 22. The distal ends 22 of the prongs 20 each include a notch 24 therein for receiving the floss 18.

Preferably, the elongated handle 12 and prongs 22 are molded integrally of a high grade, high temperature, organic polymeric material using a conventional plastic injection molding process. It will be appreciated, however, that the handle 12 and prongs 22 may be made of any other material. Similarly, the handle 12 and prongs 22 need not be made of the same material and they may comprise separate components suitably fastened together.

The dental flossing instrument 10 further includes floss manipulating means generally indicated at 26. The floss manipulating means 26 is slidably disposed on the handle 12 for movement along a second longitudinal axis L2 transverse (preferably, perpendicular) to axis L1. The floss manipulating means is movable along the axis L2 between a first retracted position P1 (FIG. 2) out of engagement with the length of floss 18 and a second extended position P2 (FIG. 3) in engagement with the length of floss 18. In the second extended position, the floss manipulating means 26 reconfigures the floss 18 from the linear configuration to a bowed configuration amenable for positioning about two sides S1,S2 and the rear R of a tooth T to be cleaned. The reconfiguration of the floss 18 will be described in greater detail below.

More specifically, the floss manipulating means 26 includes a slide member 28 slidably received in the channel 14 of the elongated handle 12 and retained therein by overturned shoulders 12a formed (e.g., molded) on the handle 12. The slide member 28 is thus free to slide along the longitudinal axis L2 within the channel 14. The retracted position of the slide member is determined by the shoulder 10b of the channel 14. In the extended position, the slide member 28 is slid to protrude out of the channel 14 as shown in FIG. 3.

Figure 2:
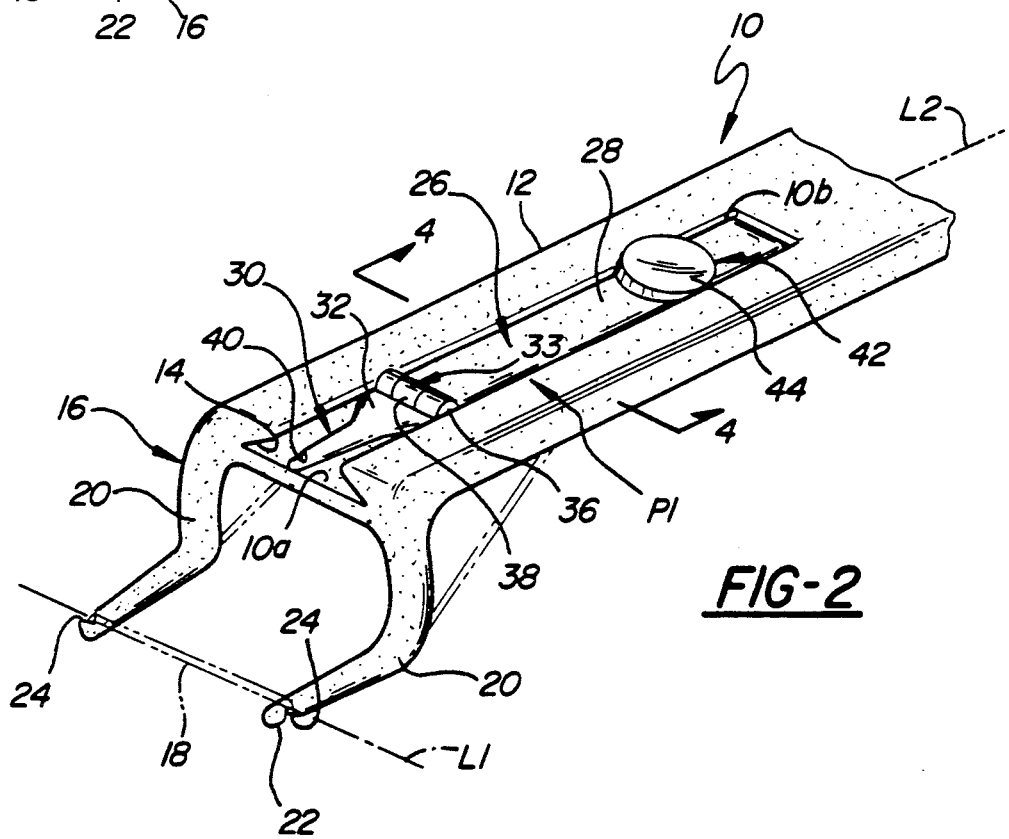
FIG. 2 is a perspective view, partially broken away, showing the slide member in the retracted position

The floss manipulating means 26 further includes floss engaging means generally indicated at 30 for engaging the length of floss 18 as the slide member 28 is moved from the first retracted position P1 toward the second extended position P2. The floss engaging means 30 comprises an elongated floss engaging member 32 pivotally secured to the slide member 28 by pivotal connection 33. The floss engaging member 32 rests on the handle 12 in the channel 14 when the slide member 28 is in the first retracted position P1 as shown in FIG. 2.

Figure 3:
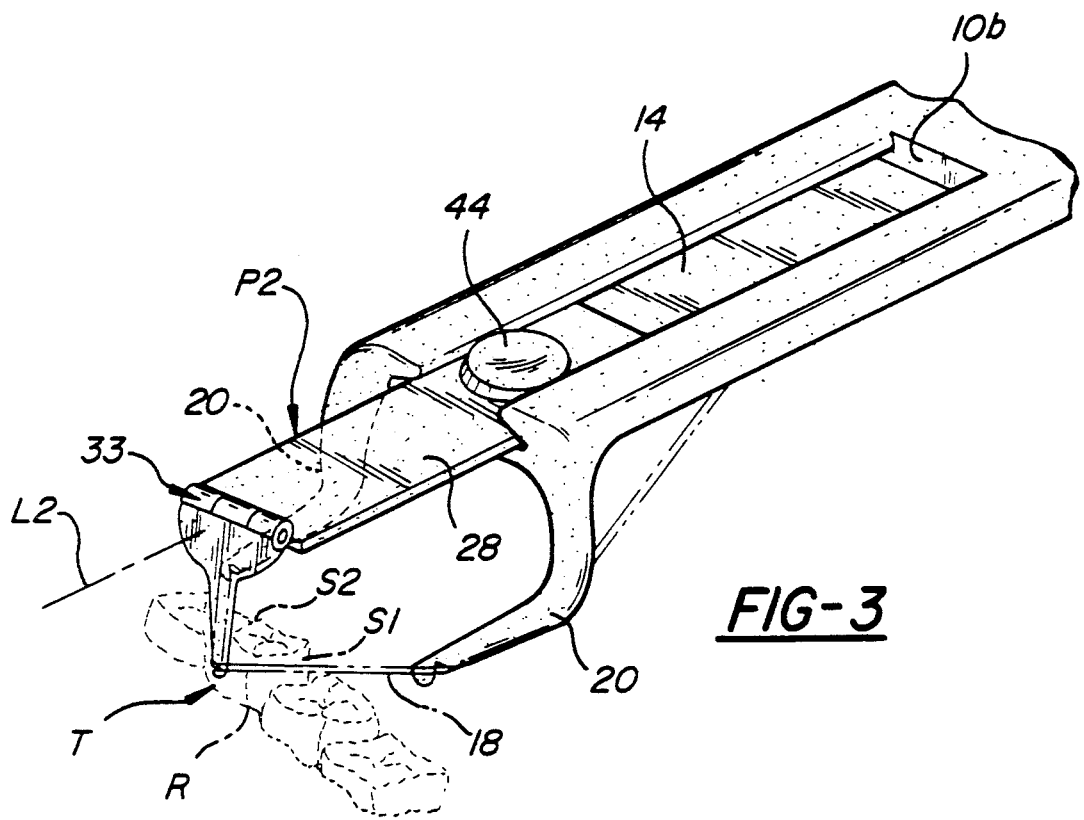
FIG. 3 is a perspective view, partially broken away, showing the slide member in the extended position.
Figure 4:
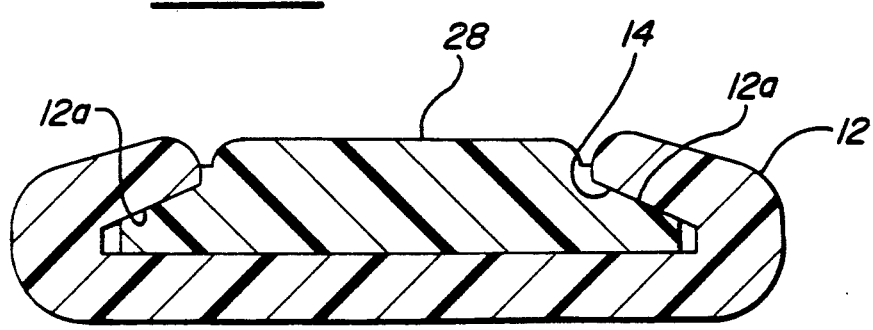
FIG. 4 is a cross-sectional view taken along lines 4—4 of FIG. 2.

As the slide member 28 is moved from the first retracted position P1 toward its second extended position P2, the floss engaging member 32 pivots of its own weight about the connection 33 to a depending position which is substantially transverse to the longitudinal axis L2 of the slide member 28 (see FIG. 3). In this depending position, the floss engaging member 32 can engage the length of floss 18 located between the prongs 20 to reconfigure it to the bowed configuration shown in FIG. 3 as the slide member 28 is further moved to the extended position P2. On the other hand, as the slide member 28 is returned to the retracted position P1 after the reconfigured length of floss is positioned about the tooth T, the floss engaging member 32 is pivoted upwardly and releases the length of floss 18 so as to leave it positioned about the tooth T.

The pivotal connection 33 between the slide member 28 and floss engaging member 32 comprises a hinge joint utilizing a hinge pin 36. The floss engaging member 32 has a mating clasp 38 integral therewith. The clasp 38 engages the hinge 36 in such a manner that the clasp 38 is free to pivot about the hinge pin 36. In this arrangement, gravity will normally bias the floss engaging member 32 to a depending position transverse to the slide member as the slide member 28 is moved toward the extended position P2. The end 10a of the handle 10 limits downward (or counterclockwise) movement of the floss engaging member 32. Alternately, hinge pins 36a are molded integral with the slide member 28 as best shown in FIG. 5 for mating with clasps 38a molded on the floss engaging member 32.

In an alternative embodiment of the invention shown in FIG. 6 (where like reference numerals primed represent like features), the slide member 28' and floss engaging member 32' are molded as one piece from a high density high molecular organic polymeric material. Polypropolyene has the requisite properties necessary to form the slide member 28' and floss engaging member 32' in this manner. It will be appreciated, however, that any other suitable material may be used.

In this alternative embodiment, a resilient "live hinge" 33' is molded between the slide member 28' and floss engaging member 32'. This "live hinge" 33' is best seen in FIG. 6. The live hinge 33' is formed integral with the slide member 28' and floss engaging member 32' as they are simultaneously molded. The "live hinge" 33' resiliently biases the floss engaging member 32' downwardly as shown in FIG. 6 as the slide member 28' is moved toward the extended position P2. As the slide member 28' is returned to the retracted position P1, a force is applied to the floss engaging member 32' by engagement of the handle end (e.g., end 10a in FIG. 1) so as to pivot the floss engaging member 32' to a position on the handle coplanar with the slide member 28'. The live hinge 33' permits only about 90° of relative movement of the floss engaging member 32' relative to the slide member 28'.

Regardless of the type of hinge mechanism employed, the floss engaging member 32 has a notch 40 therein of suitable configuration for retaining the length of floss therein as the slide member 28 is moved from the first retracted position P1 to the second extended position P2. The notch 40 is also configured to release the length of floss 18 as the slide member 28 is moved from the second extended position P2 to the first retracted position P1, thereby leaving the reconfigured floss (bowed configuration) about the tooth T. In this manner, the floss 18 can be positioned proximate the sides S1,S2 and rear R of the tooth T to be cleaned.

The slide member 28 has force receiving means generally indicated at 42 thereon. Preferably, the force receiving means 42 comprises a raised manipulating surface 44 on the slide member 28. The manipulating surface 42 is configured for manipulation by a finger of the instrument user. Preferably, the surface 44 comprises a depression or valley configuration for ergonomically receiving the user's finger. The surface 44 receives a force from the instrument user to move the slide member 28 between the first retracted position P1 and the second extended position P2.

The instrument 10 further includes floss supply means generally indicated at 46. Preferably, the floss supply means or assembly 46 is disposed on the handle 12 and functions to supply additional floss 18 between the prongs 20 may be needed to reconfigure the floss from the linear configuration to the bowed configuration. Specifically, the floss supply means comprises a spool 48 of floss 18 disposed in the hollow end of the handle 12 beneath a removal handle cover section and remote from prongs 20. The floss 18 is fed from the spool 48 through an aperture in the handle 12 to and around the upper reduced-diameter capstan 50a of a rotatable, larger diameter take-up knob 50, then to between the prongs 20, and finally to the lower end 50b of the take-up knob 50 where the end of the floss 18 is secured. The floss 18 can be fed to the prongs 20 as the length of floss is reconfigured. The knob 50 is used to maintain the floss 18 in tension to allow proper cleaning of the tooth surfaces. Such a floss spool/take-up knob arrangement 46 is known and used on dental flossers sold commercially under the designations 10561, 12011 and 12012 by Brookstone retail stores.

The length of floss 18 between the prongs 20 can be reconfigured as follows. Initially, the floss 18 is positioned in generally a linear configuration along axis L1 between the two prongs 20 (FIG. 2). In order to reconfigure the floss to the bowed configuration (FIG. 3), additional floss 18 may need to be supplied from the spool 48 or, alternately, by virtue of the prongs 20 being temporarily deflected inwardly (i.e. toward each other). With the floss 18 in the bowed configuration, the floss 18 can be positioned at the sides S1,S2 and rear R of the tooth to be cleaned.

The bowed configuration of the floss can take any of a variety of specific configurations. For instance, the bowed configuration of the floss 18 can be a V-shape (as shown in FIG. 3). If a wider, rounded floss engaging member 32 is used, the bowed configuration of the floss may be generally a U-shape. Generally, the bowed configuration includes any configuration bowed outwardly from the axis L1 to enable the length of floss 18 between prongs 20 to be positioned proximate the sides S1,S2 and rear R surface of the tooth to be cleaned.

The prongs 20 and handle 12 may include guides (not shown) thereon as needed for guiding the floss 18 from the upper capstan 50a to the notches 24 on the prongs 20 and back to the lower end 50b of the rotatable knob 50.

Operation of the instrument 10 is as follows. Initially, the instrument 10 is in the state shown in FIG. 2. In this configuration, the slide member 28 is in the retracted position P1 and is fully supported within the channel 14 of the elongated handle 12. The floss engaging member 32 extends generally parallel (i.e., coplanar) to the longitudinal axis L2 and is also supported within the channel 14 of the handle 12. The floss engaging member 32 is positioned inboard of the axis L1. The floss 18 extends from the spool 48 to the upper capstan 50a, prongs 20 and lower end 50b of the knob 50 such that the length of floss 18 lies on the axis L1 in a generally linear configuration between the prongs 20. The user positions his finger on the raised manipulating surface 44 and moves the slide member 28 from the first retracted position P (FIG. 2) toward the extended position P2 such that a portion of the slide member 28 extends outwardly from the handle 12. When the floss engaging member 32 is moved outside of or clears the end 10a of the handle 12 outside the channel 14, the floss engaging member 32 pivots downwardly to its first position (transverse to the slide member) either under the force of gravity if the hinge pin 36 is used or because of natural plastic resiliency if the "live hinge" 33' is used. The slide member 28 is advanced sufficiently outwardly until the floss engaging member 32 engages the length of floss 18 between the prongs 20 and reconfigures it to its bowed configuration, FIG. 3. Knob 50 may be rotated as needed to supply additional floss 18 and tension it. The user then positions the instrument 10 near the tooth T to be cleaned. The instrument is then manipulated relative to the tooth T so that the length of the floss 18 is positioned proximate the sides S1,S2 and rear R of the tooth to be cleaned (FIG. 3). Once the length of floss is so positioned, the user applies a force to the raised manipulating surface 44 to retract the slide member 28 from the extended position P2 to the retracted position P1. As the slide member 28 is retracted, the floss 18 slips out of the notch 40 and remains about the tooth T to be cleaned. The take-up knob 50 maintains tension on the floss 18. As the slide member 28 is moved sufficiently back toward the retracted position P1, the floss engaging member 32 engages the bottom of the channel 14. This engagement causes the floss engaging member 32 to pivot upwardly about the hinge (34,36) to a position atop the handle parallel (coplanar) to the longitudinal axis L2. With the slide member 28 in the first retracted position P1 and the floss engaging member 32 resting within the channel 14 of the handle 12, the instrument 10 can be moved upwardly and downwardly in repeated fashion to simultaneously clean between the gum and sides S1,S2 and rear R of the tooth T. This tooth cleaning process is repeated for each tooth until every tooth in the user's mouth has been cleaned sufficiently.

FIG. 7 shows an alternative embodiment of the invention wherein like reference numerals double primed represent like features of FIGS. 1-6. The alternative embodiment includes the features of the described above with respect to FIGS. 1-6, the only difference being that the prongs 20" have a slightly different configuration from those of the previous embodiment. In particular, the prongs 20" are formed to decline gradually from the end 10a" of the handle 10". Operation of the FIG. 7 embodiment is identical in all significant details.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

I claim:

1. An instrument for manipulating dental floss to allow a user to simultaneously floss three surfaces of a tooth to be cleaned, comprising:
    a handle;
    fork means extending from said handle and adapted for holding a length of floss on an axis in a generally linear configuration; and
    floss manipulating means slidably associated with said handle for movement between a first retracted position disposed inboard of said axis so as to be out of engagement with said length of floss and a second extended position disposed outboard of said axis, said floss manipulating means engaging said length of floss at a point along said linear configuration so as to reconfigure said length of floss to a bow-shaped configuration extending outboard of said axis for positioning about three surfaces of the tooth to be cleaned.

2. An instrument as set forth in claim 1 wherein said floss manipulating means comprises a slide member disposed on said handle and floss engaging means disposed on said slide member for engaging said length of floss as said slide member is moved from said first retracted position to said second extended position.

3. An instrument as set forth in claim 2 wherein said floss engaging means comprises a floss engaging member pivotally secured to said slide member so as to rest on said handle when said slide member is in said first retracted position and so as to pivot relative to said handle to (a) a position for engaging said length of floss as said slide member is moved from said first retracted position to said second extended position and (b) a position for releasing said length of floss as said slide member is moved from said extended position to said first retracted position after said length of floss is positioned about three surfaces of the tooth to be cleaned.

4. An instrument as set forth in claim 3 wherein by said floss engaging means is pivotally secured to said slide member by a live hinge.

5. An instrument as set forth in claim 3 wherein said floss engaging member is pivotally secured to said slide member by a hinge joint having a hinge pin.

6. An instrument as set forth in claim 3 wherein said floss engaging member includes a notch thereon for releasably retaining said length of floss therein as said slide member is moved from said first retracted position to said second extended position.

7. An instrument as set forth in claim 2 wherein said handle has a channel therein, said slide member being slidably received in said channel.

8. An instrument as set forth in claim 7 wherein said slide member has force receiving means thereon for receiving a force to move said slide member between said first retracted position and said second extended position.

9. An instrument as set forth in claim 8 wherein said force receiving means comprises a raised manipulating surface on said slide member, said surface being configured for manipulation by a finger of the instrument user.

10. An instrument as set forth in claim 1 further including floss supply means on said handle.

11. An instrument as set forth in claim 10 wherein said floss supply means comprises a spool of floss and a floss take-up knob on said handle.

12. An instrument as set forth in claim 1 wherein said fork means comprises a pair of spaced prongs on said handle, each of said prongs depending from said handle and extending longitudinally away therefrom to a distal end.

13. An instrument as set forth in claim 12 wherein each of said distal ends of said prongs has a notch therein adapted for maintaining said length of floss between said prongs.

14. An instrument for manipulating dental floss to a configuration that allows a user to simultaneously floss the sides and the rear of a tooth to be cleaned, comprising:
a handle;
a pair of spaced prongs extending outwardly from said handle to distal ends defining an axis therebetween along which a length of floss is positioned;
a slide member slidably disposed on said handle for movement between a first retracted position and a second extended position along a slide axis transverse to the prong-defined axis; and
a floss engaging member pivotally disposed on said slide member, said floss engaging member being oriented transverse to said slide axis and outboard of said distal ends when said slide member is in said second extended position so as to reconfigure the length of floss to said bowed configuration, and said slide member being oriented substantially parallel to said slide axis and inboard of said distal ends when said slide member is in said first retracted position.

15. An instrument for manipulating dental floss to allow a user to simultaneously floss three surfaces of a tooth to be cleaned comprising:
a handle;
fork means extending from said handle and adapted for holding a length of the floss in a generally linear configuration; and
a floss manipulating member slidably associated with said handle for movement between a first retracted position out of engagement with said length of floss and a second extended position for engagement with said length of floss so as to reconfigure said length of floss to a bow-shaped configuration for positioning about three surfaces of the tooth to be cleaned, and a floss engaging member pivotally secured to said slide member so as to rest on said handle when said slide member is in said first retracted position and so as to pivot relative to said handle to (a) a position for engaging said length of floss as said slide member is moved from said first retracted position to said second extended position and (b) a position for releasing said length of floss as said slide member is moved from said second extended position to said first retracted position after said length of floss is positioned about three surfaces of the tooth to be cleaned.

16. An instrument as set forth in claim 15 wherein said floss engaging means is pivotally secured to said slide member by a live hinge.

17. An instrument as set forth in claim 15 wherein said floss engaging member is pivotally secured to said slide member by a hinge joint having a hinge pin.

18. An instrument as set forth in claim 15 wherein said floss engaging member includes a notch thereon for releasably retaining said length of floss therein as said slide member is moved from said first retracted position to said second extended position.

* * * * *